(12) United States Patent
He et al.

(10) Patent No.: US 7,211,417 B2
(45) Date of Patent: May 1, 2007

(54) ANTIBIOTIC P175-A AND SEMISYNTHETIC DERIVATIVES THEREOF

(75) Inventors: Haiyin He, Mahwah, NJ (US); Hui Yu Yang, Tappan, NY (US); Scott William Luckman, Ringwood Borough, NJ (US); Valerie S. Bernan, New City, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 408 days.

(21) Appl. No.: 10/833,645

(22) Filed: Apr. 28, 2004

(65) Prior Publication Data

US 2004/0220195 A1 Nov. 4, 2004

Related U.S. Application Data

(60) Provisional application No. 60/467,612, filed on May 2, 2003.

(51) Int. Cl.
*A61K 31/496* (2006.01)
*C12P 17/16* (2006.01)
*C12N 1/12* (2006.01)
*C12N 1/20* (2006.01)
*C07D 401/06* (2006.01)

(52) U.S. Cl. .............. 435/118; 435/252.1; 514/253.02; 544/361

(58) Field of Classification Search ................ 544/361; 514/253.02
See application file for complete search history.

(56) References Cited

U.S. PATENT DOCUMENTS 5,994,543 A 11/1999 Shu et al.

OTHER PUBLICATIONS

He et al. Helvetica Chimica Acta, vol. 87, p. 1385-1391 (Jun. 24, 2004, online publication).*
Morbidity and Mortality Weekly; "Nosocomial Enterococci Resistant to Vancomycin"; vol. 42(30); pp. 597-599; 1993.
Handwerger, Sandra., et al.; Clin. Infect. Dis.; vol. 16; pp. 750-755; 1993.

* cited by examiner

*Primary Examiner*—Emily Bernhardt
(74) *Attorney, Agent, or Firm*—Daniel B. Moran

(57) ABSTRACT

This invention relates to a new antibiotic designated P175-A, to production of fermentation of *Micromonospora echinospora* NRRL 30633, to methods for recovery and concentration from the crude solutions, and to a process for purification and to semisynthetic esters and ethers of P175-A.

14 Claims, 4 Drawing Sheets

ANTIBIOTIC P175-A AND SEMISYNTHETIC DERIVATIVES THEREOF

"This application claims priority from provisional application No. 60/467,612 filed May 2, 2003 the entire disclosure of which is hereby incorporated by reference".

FIELD OF THE INVENTION

The invention relates to a new antibiotic, designated P175-A, and its ester and ether derivatives, to production by fermentation, to methods for recovery and concentration from the crude solutions, to a process for purification of P175-A, and to synthesis of its derivatives. The present invention includes within its scope the agents in dilute forms, as crude concentrates, and in pure form. The present invention also relates to the use of compounds according to the invention in antimicrobial compositions such as antiseptics, disinfectants or preservatives.

BACKGROUND OF THE INVENTION

Bacterial resistance to antibiotics is a serious public health problem. In hospitals, vancomycin-resistant isolates are becoming more common. A recent survey found 7.9% of *Enterococci* in United States hospitals are now vancomycin-resistant. "Nosocomial *Enterococci* Resistant to Vancomycin" Morbidity and Mortality Weekly Report 42(30):597–598(1993). Further resistance of Vancomycin and other antibiotics to *Enterococcus faecium* is reported, Handwergers. et al., Clin. Infect. Dis. 1993(16),750–755. Resistance organisms are also a problem for other important antibiotics which includes piperacillin. Clearly, antibiotic resistance is a growing public health problem and having new antibiotics available could provide additional options for physicians in treatment regimens.

The medical community recognizes that there is an ongoing need for additional antibiotics. The search for new antibiotics which exhibit antibacterial activity against vancomycin-resistant isolates and having structures which are not derivatives of vancomycin are particularly appealing.

Bravomicins, as antibacterial agents are described in U.S. Pat. No. 5,994,543

The above disclosed bravomicins are distinct from the antibacterial agents disclosed in the present invention.

BRIEF SUMMARY OF THE INVENTION

The present invention relates to compounds of Formula I

Formula I

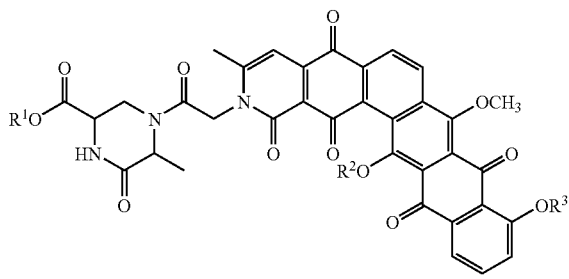

wherein:

R$^1$ is H, straight or branched alkyl of 1 to 10 carbon atoms, cycloalkyl of 3 to 10 carbon atoms,

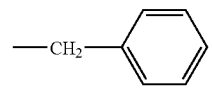

or —CH$_2$COOR$^4$;

R$^2$ and R$^3$ are independently H or —CH$_2$CO$_2$R$^4$;

R$^4$ is H or straight or branched alkyl of 1 to 10 carbon atoms and pharmaceutically acceptable salts thereof.

The present invention in particular relates to the antibiotic P175-A. The structure of the antibiotic P175-A is:

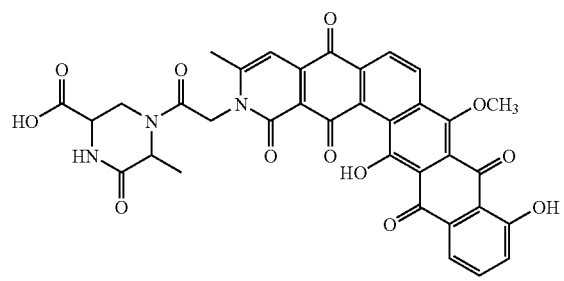

and pharmaceutically acceptable salts thereof.

The present invention includes within its scope the antibiotics of Formula I in dilute form, as a crude concentrate, and in pure form. The present invention also relates to the use of the compounds according to the invention in antimicrobial compositions and as an antiseptic, or disinfectant. In particular, the present invention includes within its scope the antibiotic P175-A in dilute form, as a crude concentrate, and in pure form.

It is an embodiment of this invention to provide compounds of formula I of the invention, which are shown to possess antibacterial activity, especially against vancomycin resistant bacterial isolates and in particular having a chemical structure unlike vancomycin.

It is a further embodiment of the invention to provide a method of treating bacterial infections in mammals in need thereof with an effective amount of the compound P175-A and pharmaceutically acceptable salts thereof.

It is an additional embodiment of the invention to provide a pharmaceutical composition of P175-A and pharmaceutically acceptable salts thereof in the presence of one or more pharmaceutically acceptable carriers.

It is a further embodiment of the invention to provide a process for the preparation of esters of P175-A.

DESCRIPTION OF THE PREFERRED EMBODIMENTS

An embodiment within the scope of this invention relates to novel compounds of Formula I.

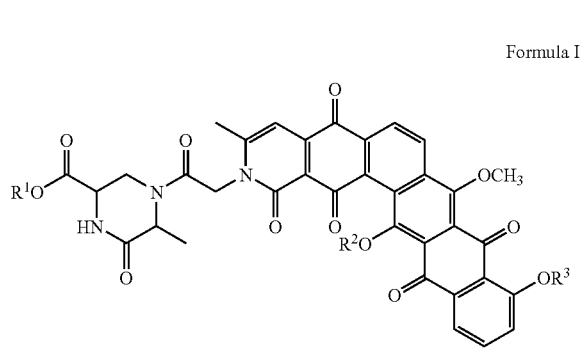

Formula I wherein:

R$^1$ is H, straight or branched alkyl of 1 to 10 carbon atoms, cycloalkyl of 3 to 10 carbon atoms,

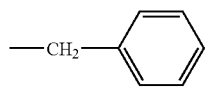

or —CH$_2$COOR$^4$;

R$^2$ and R$^3$ are independently H or —CH$_2$CO$_2$R$^4$;

R$^4$ is H or straight or branched alkyl of 1 to 10 carbon atoms.

Preferred embodiments of formula I of the invention include:

a): R$^1$ is —CH$_3$, —CH$_2$CH$_3$, —CH(CH$_3$)$_2$, or

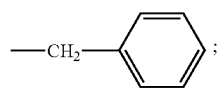

and

R$^2$ and R$^3$ are H;

b) R$^1$ is H, or —CH$_2$COOCH$_3$;

R$^2$, and R$^3$ are independently H, or —CH$_2$COOCH$_3$; and c) R$^1$ is H;

R$^2$ and R$^3$ are independently H, or —CH$_2$COOH.

A further preferred embodiment of the invention relates to new antibiotic P175-A, to the production of the antibiotic by fermentation, to methods for the recovery and concentration of the antibiotic from crude solutions, and to processes for the purification of the antibiotic. The invention includes within its scope the new antibiotic in diluted form, as crude concentrate and in pure form. The novel antibiotic is useful as an antibacterial agent.

The structure of the new antibiotic P175-A is:

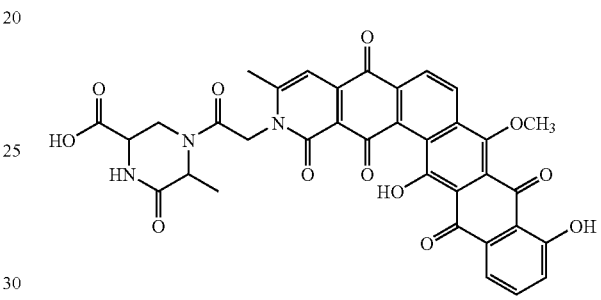

Figure 1:
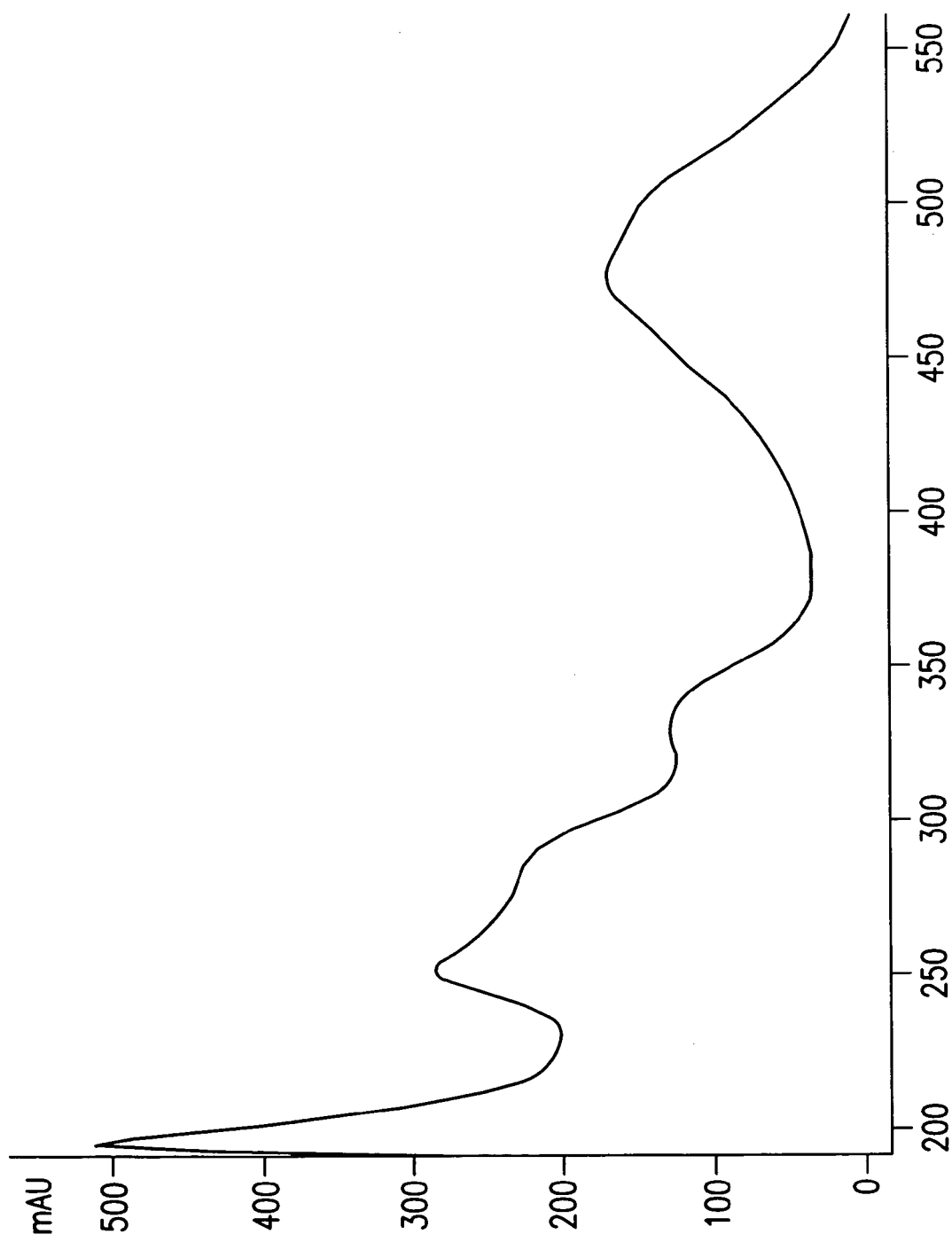
FIG. 1 shows ultraviolet absorption spectrum of P175-A (1:1 MeCN/H$_2$O)
Figure 2:
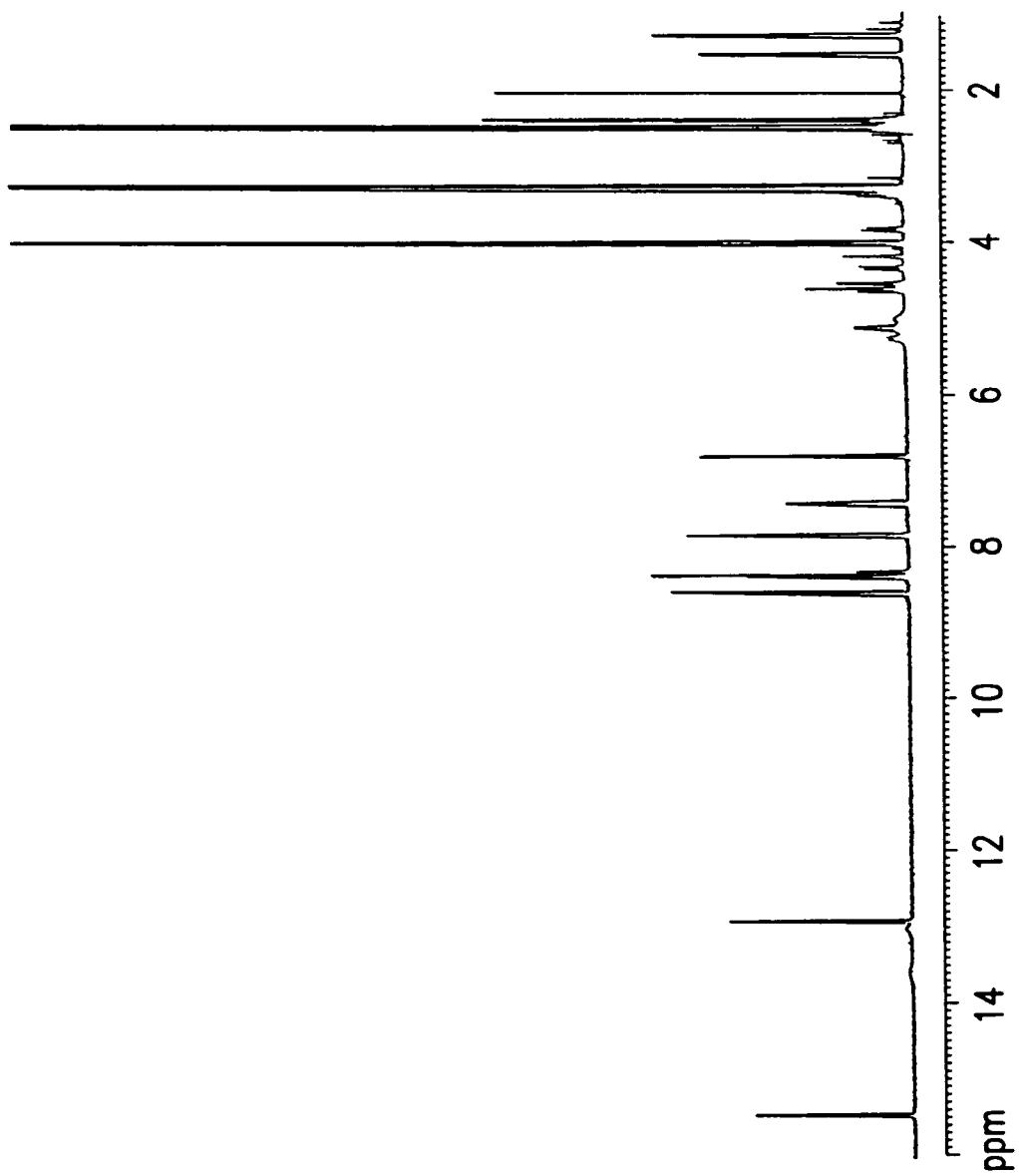
FIG. 2 shows proton nuclear magnetic resonance spectrum P175-A at 25° C. (400 MHz, DMSO-d$_6$)
Figure 3:
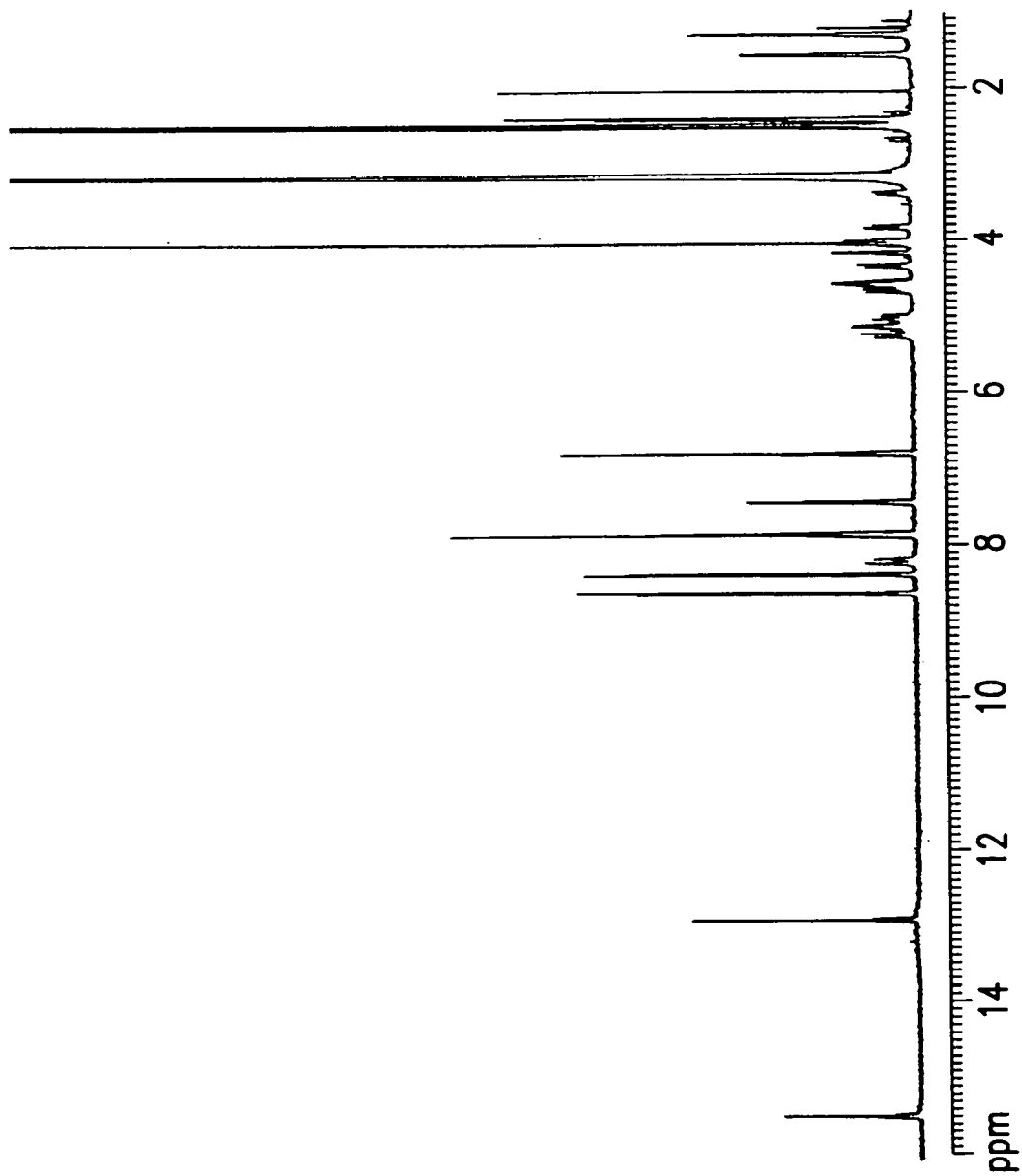
FIG. 3 shows proton nuclear magnetic resonance spectrum P175-A at 55° C. (400 MHz, DMSO-d$_6$)
Figure 4:
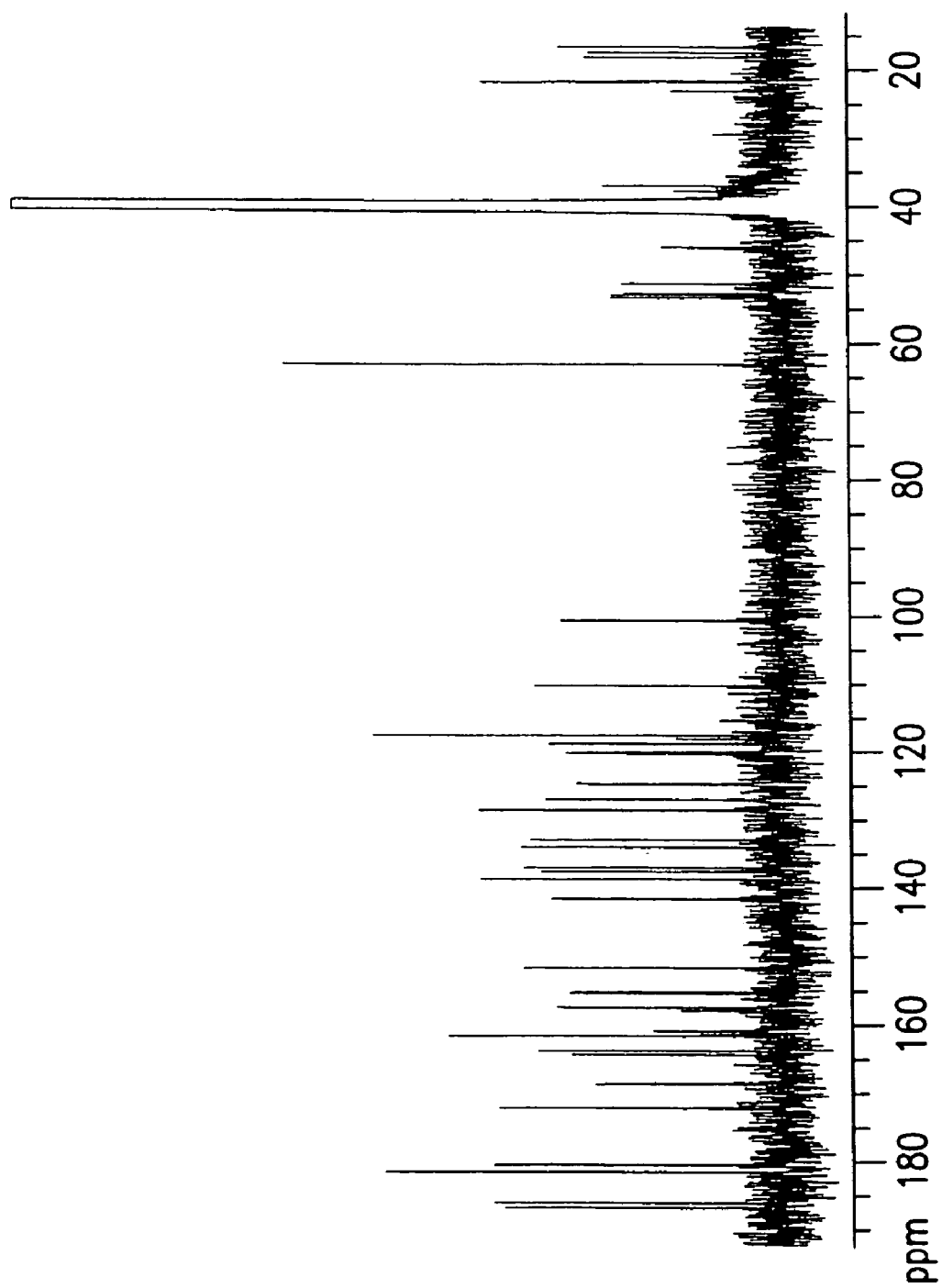
FIG. 4 shows carbon-13 nuclear magnetic resonance spectrum P175-A at 25° C. (100 MHz, DMSO-d$_6$).

The physico-chemical characteristics of P175-A are as follows:

1. Molecular weight: 679 (ESIMS);
2. Apparent molecular formula: C$_{35}$H$_{25}$N$_3$O$_{12}$;
3. High-resolution Fourier transform ion cyclotron resonance mass spectrum (positive): m/z 680.15251 (MH$^+$, C$_{35}$H$_{26}$N$_3$O$_{12}$ requires 680.15109); High-resolution Fourier transform ion cyclotron resonance mass spectrum (negative): m/z 678.13647 (MH$^-$, C$_{35}$H$_{24}$N$_3$O$_{12}$ requires 678.13654);
4. Ultraviolet absorption spectrum as shown in FIG. 1 (1:1 MeCN/H$_2$O);
5. Proton nuclear magnetic resonance spectrum at 25° C. as shown in FIG. 2 (400 MHz, DMSO-d$_6$);
6. Proton nuclear magnetic resonance spectrum at 55° C. as shown in FIG. 3 (400 MHz, DMSO-d$_6$);
7. Carbon-13 nuclear magnetic resonance spectrum at 25° C. as shown in FIG. 4 (100 MHz, DMSO-d$_6$), with significant signals listed below:

| | | | | |
|---|---|---|---|---|
| 187.189 | 186.480 | 181.948 | 180.807 | 172.296 |
| 168.763 | 168.530 | 164.429 | 163.866 | 161.757 |
| 161.008 | 157.714 | 157.658 | 155.623 | 155.404 |
| 151.787 | 141.557 | 141.490 | 138.540 | 137.437 |
| 136.868 | 133.849 | 132.737 | 128.398 | 126.785 |
| 124.647 | 124.425 | 120.100 | 119.901 | 119.787 |
| 118.535 | 117.749 | 117.318 | 110.082 | 100.524 |
| 62.740 | 53.096 | 52.697 | 52.555 | 50.953 |
| 45.567 | 45.577 | 40.400 | 37.292 | 21.204 |
| 21.041 | 17.458 | 15.954 | | |

The new antibiotic, designated P175-A is formed during the cultivation under controlled conditions of *Micromonospora echinospora* strain designated P175.

This microorganism is maintained in the culture collection of Wyeth Research, Pearl River, N.Y. 10965, as culture P175. A viable culture of this microorganism is deposited under the Budapest Treaty with the Patent Culture Collection Laboratory, Northern Regional Research Center, U.S. Department of Agriculture, Peoria, Ill. 61604, and added to its permanent collection. Culture P175 has been assigned the NRRL accession # 30633.

The 16S rDNA sequence is determined for strain P175 following isolation and direct sequencing of the amplified gene. The 16S rDNA sequence is compared to databases by the use of BLAST (Basic Local Alignment Search Tool) to determine the phylogenetic position and phylogenetic trees are generated by using two neighbour-joining tree algorithms. The 16S rDNA sequence supported classification of the strain in the genus and species of *Micromonospora echinospora*.

Culture P175 was isolated from a soil sample obtained in Ventura, Calif. Observations were made of the cultural, physiological and morphological features of culture P175 using methods well known in the art. The macromorphology for culture P175 is described in Table 1

TABLE 1

Cultural characteristics of streptomycete strain P175

| Agar Medium | P175 |
| --- | --- |
| Yeast-malt (ISP2) | G: Rapid and abundant<br>SM: Dark grey red brown (47)<br>SP: None |
| Oatmeal (ISP3) | G: Moderate<br>SM: Medium red brown (43)<br>SP: None |
| Inorganic salts-starch (ISP4) | G: Very Abundant<br>SM: Dark red brown (44)<br>SP: None |
| Glycerol-Asparagine agar (ISP5) | G: Sparse<br>SM: Light grey red brown (45)<br>SP: None |

G, growth;
SM, substrate mycelium;
SP, soluble pigment
ISCC, National Bureau of Standard Centroid Color Charts, Publication 440, Washington, D.C. 1976.

Culture P175 produces no aerial mycelium. Spores at maturity are spherical, 1.0–1.5 μm in diameter and covered with blunt spines. Sporophores are mostly solitary, but occasionally in small clusters on the same hyphae. Spores are never observed in chains. Spore layer is black and waxy to dry rather than moist or viscid. Microscopic observations indicate that the mycelia range from 0.4 to 0.8 μm in diameter and are sparsely branched.

Physiological studies from culture P175 resulted in no melanin production, good starch hydrolysis, decomposition and fair growth on cellulose, good nitrate production, no growth on tyrosine and peptone iron agar, and no gelatine liquification. Carbohydrate utilization tests indicated good growth on: D-glucose, L-arabinose, cellulose, mannose, sucrose, D-xylose; moderate growth on D-galactose, D-mannitol; and no growth on I-inositol, α-L rhamnose, raffinose. Culture P175 exhibited abundant growth at 22° C., 28° C., and 37° C., but no growth at 45° C. and 50° C.

On the basis of the above properties, culture P175 is most similar to the properties of *Micromonospora echinospora* ATCC 15837. A comparison of culture P175 to *Micromonospora echinospora* ATCC 15837 revealed several different characteristics. Analysis of the ISP carbon utilization tests revealed that culture P175 had moderate growth on galactose and mannitol, but no growth on raffinose, in comparison to *Micromonospora echinospora* ATCC 15837 which had abundant growth on raffinose and galactose, but no growth on mannitol. *Micromonospora echinospora* ATCC 15837 also exhibited good growth on tyrosine and peptone-iron agar, but culture P175 had little or no growth on these substrates. Other differences include culture P175 cannot liquify gelatin and demonstrates good nitrate reduction, *Micromonospora echinospora* ATCC 15837 can liquify gelatine and nitrate reduction is variable. These differences support the creation of a new strain of *M. echinospora* P175.

For the production of the new antibiotic P175-A, the present invention is not limited to this particular organism or to organisms fully answering the above characteristics, which are given for illustration purposes only. It is desired and intended to include the use of mutants produced from this organism by various means such as exposures to X-radiation, ultraviolet radiation, N'-methyl-N'-nitro-N-nitrosoguanidine, phages, and like.

General Alkylation Method in Production of Compounds with Formula I

The alkylation of P175-A with excess amount of an alkylating reagent $R^1X$ where X is bromo or iodo which includes bromoacetate methyl ester ($BrCH_2COOCH_3$) in the presence of a base such as sodium carbonate, preferably in dimethylsulfoxide (DMSO) affords a mixture of products of Formula I. The individual components, purified from the mixture, are then optionally hydrolyzed to afford ethers of Formula I by an aqueous solution containing 5% (w/v) sodium carbonate.

The alkylation of P175-A with an excess amount of bromoacetate methyl ester ($BrCH_2COOCH_3$) in the presence of sodium carbonate affords a mixture of esters 1, 2 and 4 of formula I. Esters 2 and 4 purified from the mixture are each independently hydrolyzed by an 1:1 $MeCN/H_2O$ solution containing 2.5% (w/v) sodium carbonate to afford ethers 3 and 5 of Formula I as shown in Scheme I.

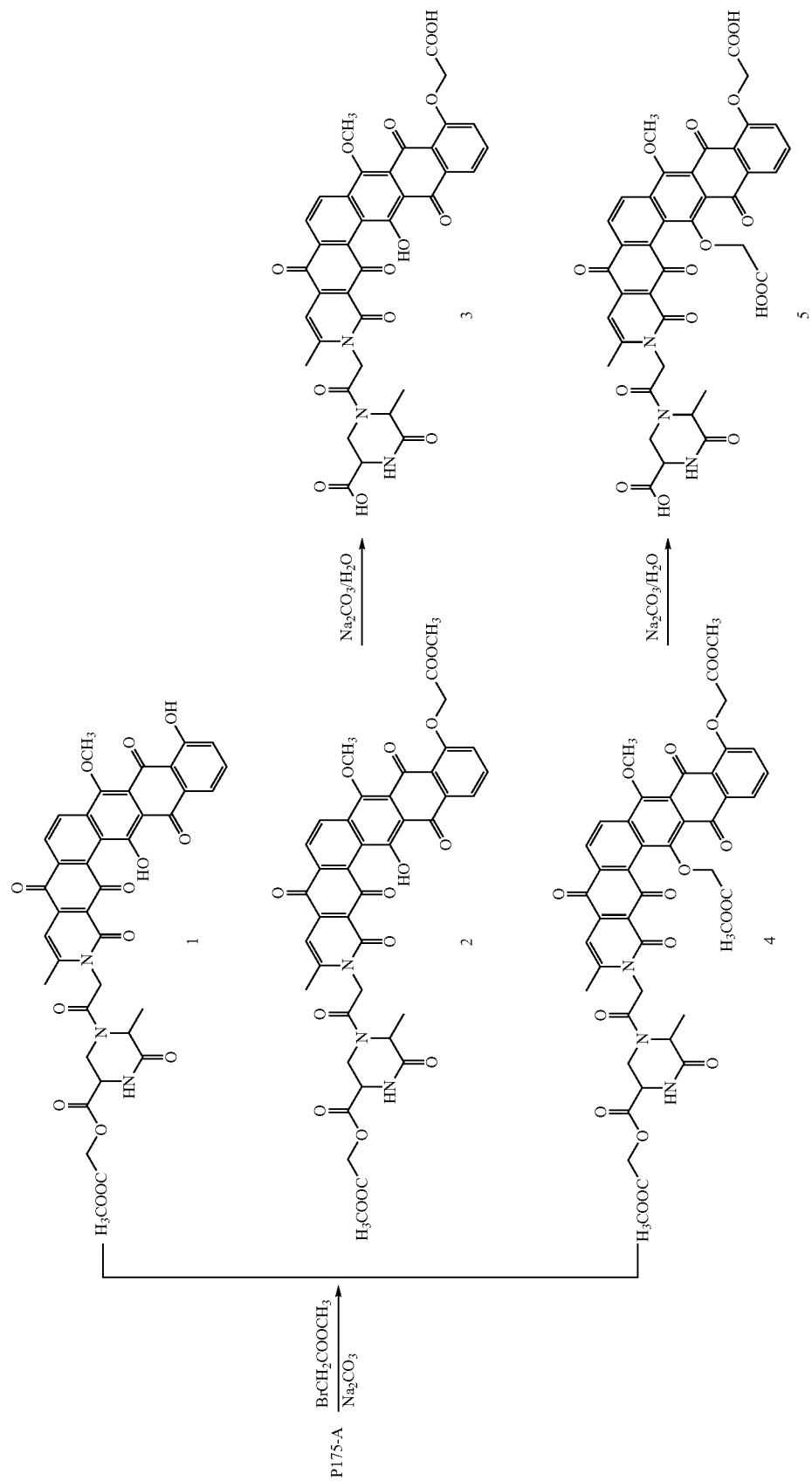
Scheme I

The esterification of P175-A with an alkyl bromide or iodide in dimethylsulfoxide in the presence of sodium carbonate affords an ester derivative 6 of Formula I. Additionally, esters of Formula I where $R^1$ is a straight, branched, or cyclic alkyl group containing 1–10 carbons, or

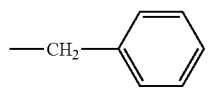

may be prepared by using an appropriate alkylating agent which includes $R^1X$ where X is bromo or iodo in the presence of a base which includes sodium carbonate as shown in Scheme II.

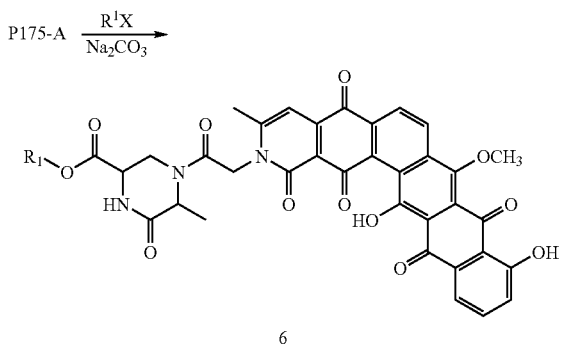

Scheme II

6

Biological Activity

The minimal inhibitory concentration (MIC), the lowest concentration of the antibiotic which inhibits growth of the test organism, is determined by the broth dilution method using Muller-Hinton II agar (Baltimore Biological Laboratories) following the recommendations of the National Committee for Clinical Laboratory Standards [Methods for dilution antimicrobial susceptibility tests for bacteria that grow aerobically. Approved standard M7-A2. National Committee for Clinical Laboratory Standards, Villanova, Pa.].

An inoculum level of $5 \times 10^5$ CFU/ml, and a range of antibiotic concentrations (64–0.06 μg/ml) is used. The MIC is determined after the microtiter plates are incubated for 18 hours at 35° C. in an ambient air incubator. The test organisms comprise a spectrum of the Gram-positive bacteria *Staphylococcus aureus, Streptococcus pneumoniae,* and *Enterococcus* sp., the Gram-negative bacteria *Escherichia coli,* and the yeast *Candida albicans.* These organisms include recent clinical isolates that are resistant to methicillin and vancomycin. MIC data of P175-A and esters of formula I are listed in Table 1, and ethers of Formula I are listed in Table 2.

The in vitro antimicrobial results show that the new antibiotics according to the invention have significant activity against Gram-positive bacteria tested.

Antibiotic P175-A, and compounds of Formula I, derive utilities from their antibacterial activity. For example, these compounds may be used in suppression of bacterial infections, as topical antibacterial agents and as general disinfectants for laboratories.

TABLE 1

Antimicrobial activity of P175-A and its ester derivatives with Formula I.

| | MIC (μg/ml) P175-A Formula I (ester) | | | | |
|---|---|---|---|---|---|
| Test organism | Example 3 | Example 4 | Example 5 | Example 6 | Example 7 |
| *Staphylococcus aureus* (3 strains, including a methicillin-resistant strain) | <0.06–0.25 | <0.06–0.12 | <0.06–0.12 | 1–4 | 0.12–2 |
| *Enterococcus faecalis* (2 strains, including a vancomycin-resistant strain) | <0.06 | <0.06 | 0.25–0.5 | 4 | 2–8 |
| *Streptococcus pneumoniae* GC 1894* (5% LHB) | 16 | 1 | 0.5 | 2 | 0.5 |
| *Streptococcus pneumoniae* GC 1894+ (THY) | 8 | 2 | 1 | 4 | 0.25 |
| *Bacillus subtilis* | 0.12 | 0.12 | 0.25 | 8 | 4 |
| *Escherichia coli* | >64 | >64 | >64 | >64 | >64 |
| *Escherichia coli* (imp) | 8 | 4 | 16 | 16 | 32 |
| *Candida albicans* | >64 | >64 | >64 | >64 | >64 |

TABLE 2

Antimicrobial activity of P175-A ether derivatives of Formula I.

| | MIC (μg/ml) | | | | |
|---|---|---|---|---|---|
| Test organism | Example 8A | Example 8B | Example 8C | Example 9D | Example 9E |
| *Staphylococcus aureus* (3 strains, including a MRSA) | 0.5–2 | 64->64 | >64 | 8–16 | 64 |

TABLE 2-continued

Antimicrobial activity of P175-A ether derivatives of Formula I.

| | MIC (μg/ml) | | | | |
|---|---|---|---|---|---|
| Test organism | Example 8A | Example 8B | Example 8C | Example 9D | Example 9E |
| *Enterococcus faecalis* (2 strains, including a VRE) | 0.5–1 | 64 | >64 | 8 | >64 |
| *Streptococcus pneumoniae* GC 1894* (5% LHB) | 64 | >64 | 64 | >64 | >64 |
| *Streptococcus pneumoniae* GC 1894+ (THY) | 64 | >64 | 64 | 64 | 64 |
| *Bacillus subtilis* | 1 | >64 | >64 | 8 | >64 |
| *Escherichia coli* | >64 | >64 | >64 | >64 | >64 |
| *Escherichia coli* (imp) | 8 | >64 | >64 | >64 | >64 |
| *Candida albicans* | >64 | >64 | >64 | >64 | >64 |

For the production of the new antibacterial agent P175-A the present invention is not limited to this particular organism. In fact, it is desired and intended to include the use of naturally-occurring mutants of this organism, as well as induced mutants produced from this organism by various mutagenic means known to those skilled in the art, such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques known to those skilled in the art such as for example, conjugation, transduction and genetic engineering techniques.

It is understood that this invention encompasses all crystalline forms of compounds of this invention and their pharmaceutically acceptable salts.

As used herein, the pharmaceutically acceptable salts of compounds of the invention where a carboxyl group is present, prepared by the processes of this invention may be formed with bases such as alkali metals (Na, K, Li) or alkaline earth metals (Ca or Mg).

The in vitro antimicrobial results show that the products according to the invention have significant activity against Gram-positive bacteria tested.

Antibiotic P175-A and compounds of Formula I derive their utility from antibacterial activity. For example, P175-A and compounds of Formula I may be used in the suppression of bacterial infections, as topical antibacterial agents or as a general disinfectant. P175-A and compounds of Formula I are not limited to the uses listed. In therapeutic use, compounds of this invention may be administered in the form of conventional pharmaceutical compositions appropriate for the intended use. Such compositions may be formulated as to be suitable for oral, parenteral or topical administration. The active ingredient may be combined in admixture with a nontoxic pharmaceutical carrier that may take a variety of forms depending on the form of preparation desired for administration, i.e. oral, parenteral, or topical.

When the compounds of the invention are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight. An effective amount of compound from 0.01 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the antibiotic of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotic of the invention.

The active compound of the invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The active compound may also be administered parenterally or intraperitoneally. Solutions or suspensions of the active compound as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition, which comprises a compound of this invention in combination or association with a pharmaceutically acceptable carrier. In particular, the present invention provides a pharmaceutical composition, which comprises an antibacterially effective amount of a compound of this invention and a pharmaceutically acceptable carrier.

The present invention further provides a method of treating bacterial infections in warm-blooded animals including man, which comprises administering to the afflicted warm-blooded animals an antibacterially effective amount of a compound or a pharmaceutical composition of a compound of the invention. The invention will be more fully described in conjunction with the following specific examples, which are not to be construed as limiting the scope of the invention.

As used herein an effective amount refers to the quantity of a compound of the invention which is sufficient to yield a desired therapeutic response without undue adverse side effects (such as toxicity) commensurate with a reasonable benefit/risk ratio when used in the method of this invention.

P175-A and compounds of Formula I according to the invention, have good antimicrobial activity may be used in antimicrobial compositions, especially as an antiseptic by local and general application, and as a disinfectant.

As antiseptics for human or veterinary use, the concentration of active product can vary from about 0.01% to 5% by weight according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing P175-A and compounds of Formula I according to the invention are obtained using amphoteric, anionic, cationic or non-ionic surfactants at a concentration of about 0.3 to 30%, humectants such as glycols or polyethylene glycols, at a concentration of 0 to 20% ethylene oxide and polypropylene copolymers at a concentration of 0 to 20%, and an alcohol (ethanol, isopropanol, benzyl alcohol) or a polyol, such as glycerol, at a concentration of 0 to 15%, as well as agents for complexing $Ca^{++}$, $Mg^{++}$ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra monoethanolamide or diethanolamide, fragrances, preservatives and colorants.

It is possible to use microemulsions, micellar solutions or any other phase of the ternary or quaternary diagram of water/active principle/surfactant/co-surfactant which permits solubilization of P175-A and compounds of Formula I in water. These solutions can be used in diluted or undiluted form and can be dispensed for example by means of a vasopump or liquefied or non-liquefied propellants.

With the same constituents at appropriate concentrations, the product according to the invention can also be used to prepare simple aqueous solutions or aqueous solutions in the form of sprays for making operative fields antiseptic, for postoperative treatments, for the treatment of burns, superinfected eczema, gluteal erythema, wounds or acne, or for deodorants.

Simple alcoholic solutions or alcoholic solutions in the form of sprays containing 20 to 80% by weight of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefosse). These solutions are to be used for making the skin antiseptic before puncture, for preparing the operative field, by nursing staff for making their hands antiseptic and for treating closed infected dermatosis, folliculitis, perionychia or acne.

P175-A and compounds of Formula I according to the invention can be applied in the form of creams together with the fatty substances normally found in the preparation of creams or emulsions.

P175-A and compounds of Formula I according to the invention can also be used in animals for indications such as the prevention or treatment of infected lesions. In this case, the pharmaceutical compositions are similar to those used in man, in particular creams sprays or solutions.

Moreover, the rapid lethal action on germs of P175-A and compounds of Formula I according to the invention may be used as surface disinfectants at concentrations which can vary from about 0.1 to 4% by weight. In this case, P175-A and compounds of Formula I are used in preparations such as aqueous or non-aqueous foaming detergent solutions, sprays or nebulizers. This type of preparation is particularly useful in the hospital or veterinary sectors. These preparations can contain the same constituents as those used in the antiseptic formulations, although a variety of organic solvents may be added.

General Fermentation Conditions

Cultivation of *Micromonospora* sp. designated LL-P175 may be carried out in a wide variety of liquid culture media. Media which are useful for the production of P175-A include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

General Isolation Procedures of Antibiotic P175-A

The P175-A is recovered from the fermentation broth by extracting whole broth with n-butanol. Upon concentration, the n-butanol extract is redissolved in a small quantity of dimethylsulfoxide DMSO and the dark colored solution was precipitated by adding 1:1 methanol/water. The precipitate obtained by centrifugation is chromatographed by reversed phase HPLC on C18 columns using acidic acetonitrile in water to afford the new antibiotic P175-A.

The invention is further described in conjunction with the following non-limited examples.

EXAMPLE 1

Seed Preparation

Culture Preservation

Culture P175 is preserved as frozen whole cells (frozen vegetative mycelia, FVM) prepared from cells grown for 72 hours in ATCC medium 172 (Dextrose 1%, Soluble Starch 2%, Yeast Extract 0.5%, and N-Z Amine Type A 0.5%, $CaCO_3$ 0.1% pH 7.3). Glycerol is added to 20% and the cells are frozen at −150° C.

Cultivation

Media useful for the cultivation of P175 and the production of the new antibiotic P175-A include assimilable carbon sources such as dextrose, sucrose, glycerol, molasses, starch, etc; an assimilable source of nitrogen such as ammonium chloride, amino acids, protein hydrolysates, corn steep liquor, etc; and inorganic anions and cations such as potassium, sodium, sulfate, calcium, magnesium, chloride, etc. Trace elements such as zinc, cobalt, iron, boron, molybdenum, copper, etc., are supplied as impurities of other constituents of the media. Aeration in tanks and bottles is supplied by forcing sterile air through or onto the surface of the fermenting medium. A mechanical impeller provides further agitation in tanks. An antifoam agent such as but not limited to polypropylene glycol may be added as needed.

Seed Preparation

A seed medium of the following formulation is prepared:

| | |
|---|---|
| Dextrose | 1.0% |
| Soluble starch | 2.0% |
| Yeast extract | 0.5% |
| N-Z Amine Type A (Sheffield) | 0.5% |
| CaCO3 | 0.1% |
| pH | 7.3 |

Seed medium (8 ml) in four 25 mm×150 mm glass culture tubes are inoculated with cells of LL-P175 cultured on ATCC agar medium #172 (ATCC Media Handbook, 1$^{st}$ edition, 1984). Sufficient inoculum from the agar culture is used to provide a turbid seed after 72 hours of growth. The primary seed tubes are incubated at 28° C., 200 rpm using a gyro-rotary shaker with a 2 inch throw, for 72 hours. The primary seed (~16% inoculum) is then used to inoculate four 250-ml Erlenmeyer flasks containing 50 ml of medium #172. These secondary seed flasks are incubated at 28° C., 200 rpm using a gyro-rotary shaker (2" stroke), for 72 Hours.

EXAMPLE 2

Fermentation

A fermentation production medium of the following formulation is prepared:

| | |
|---|---|
| Glycerol | 1.0% |
| Soy Peptone | 0.5% |
| K2HPO4 | 0.25% |
| NaCl | 0.5% |
| Magnesium Sulfate - 7H2O | 0.05% |
| KCl | 0.05% |
| Agar | 0.04% |
| PH | 7.0 |

A 7.5-L glass jar fermentors are prepared with 5.0 L of the above production medium and inoculated with 200 ml (4.0%) of the secondary seed fermentation and incubated at 28° C. for 6 days at 300 rpm with 5.0 L/min airflow. The fermentation as described was then allowed to proceed for approximately 168 hours and harvested for further isolation of P175-A.

EXAMPLE 3

Purification of New Antibiotic P175-A

EXAMPLE 3
PURIFICATION OF NEW ANTIBIOTIC P175-A

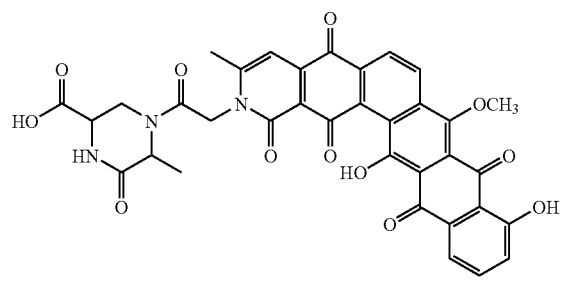

The whole broth obtained in EXAMPLE 2 is centrifuged at 3800 rpm and the supernatant extracted by n-butanol (1L). The organic layer is evaporated under reduced pressure to obtain a brownish gum, which is then dissolved in dimethylsulfoxide (DMSO, 100 ml). The solution is poured into a mixed solvent of 1:1 methanol/water (1 L). The precipitate, obtained by centrifugation, is then dissolved in a small volume of DMSO and chromatographed by reversed phase HPLC on a C18 column (YMC ODS-A, 10 μm particle size, 70×500 mm in size), using a linear gradient of 30–100% acetonitrile in water containing 0.01% trifluoroacetic acid (TFA) over 35 min. The fraction at 22 minutes, monitored by UV detection at 460 nm, is evaporated to afford pure P175-A (45 mg) as a pink amorphous powder.

EXAMPLE 4

P175-A Method Ester

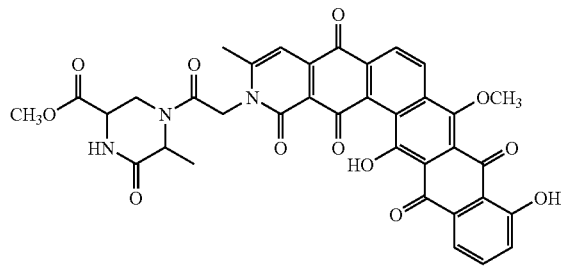
EXAMPLE 4
P175-A METHYL ESTER

To a solution of P175-A (100 mg) in anhydrous DMSO (2.5 ml), is added sodium carbonate (200 mg) and then methyl iodide (138 μl). The reaction mixture is stirred at room temperature for 2 hours. The resulting mixture is filtered. The filtrate is acidified with TFA and then chromatographed by HPLC on the same C18 column as in EXAMPLE 3, using a linear gradient (50–100% acetonitrile in water containing 0.01% TFA in 35 minutes) to afford P175-A methyl ester (32.2 mg, Formula I, R=CH$_3$). ESIMS (positive) m/z 694 (M+H)$^+$.

EXAMPLE 5

P175-A Ethyl Ester

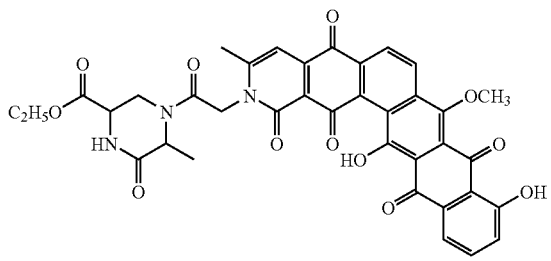
EXAMPLE 5
P175-A ETHYL ESTER

P175-A (50.0 mg) is esterified using ethyl iodide (89 μl) to replace methyl iodide in the procedure described in EXAMPLE 4 to afford P175-A ethyl ester (12.4 mg, Formula I, R=CH$_2$CH$_3$). ESIMS (positive) m/z 708 (M+H)$^+$.

EXAMPLE 6

P175-A Isopropyl Ester

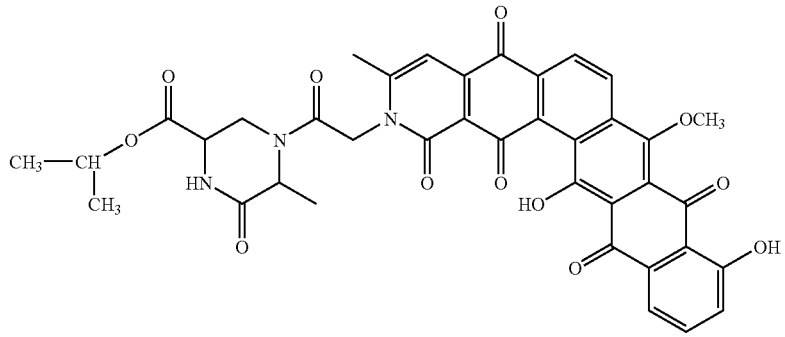
EXAMPLE 6
P175-A ISOPROPYL ESTER

To a solution of P175-A (50 mg) in anhydrous DMSO (2.0 ml), is added sodium carbonate (100 mg) and then isopropyl bromide (104.2 μl). The reaction mixture is heated at 60° C. for 1 hour. The resulting mixture is filtered. The filtrate is acidified with TFA and is then chromatographed by HPLC on the same C18 column using a linear gradient (65–100% acetonitrile in water containing 0.01% TFA in 18 minutes) to afford P175-A isopropyl ester (3.6 mg, Formula I, R=CH(CH$_3$)$_2$). ESIMS (positive) m/z 722 (M+H)$^+$.

EXAMPLE 7

P175-A Benzyl Ester

EXAMPLE 7
P175-A BENZYL ESTER

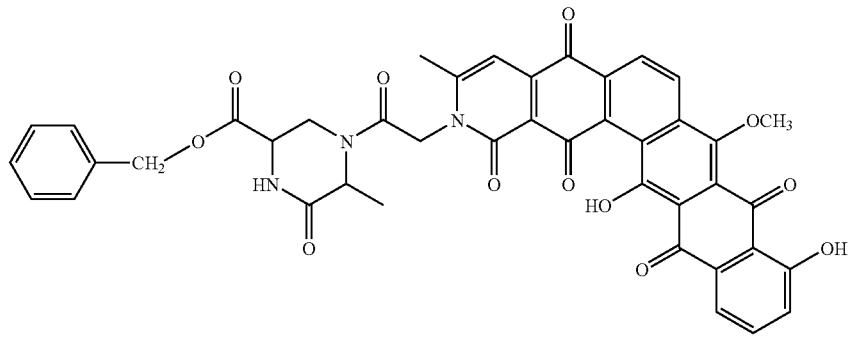

To a solution of P175-A (100 mg) in anhydrous DMSO (2.5 ml), is added sodium carbonate (200 mg) and then benzyl bromide (264 μl). The reaction mixture is stirred at room temperature for 5 hours. The resulting mixture is filtered. The filtrate is acidified with TFA and then chromatographed by HPLC on the same C18 column using a linear gradient (80–100% acetonitrile in water containing 0.01% TFA in 35 minutes) to afford P175-A benzyl ester (24.5 mg, Formula I, R=CH$_2$C$_6$H$_5$). ESIMS (positive) m/z 770 (M+H)$^+$.

EXAMPLES 8A, 8B and 8C

Example 8A

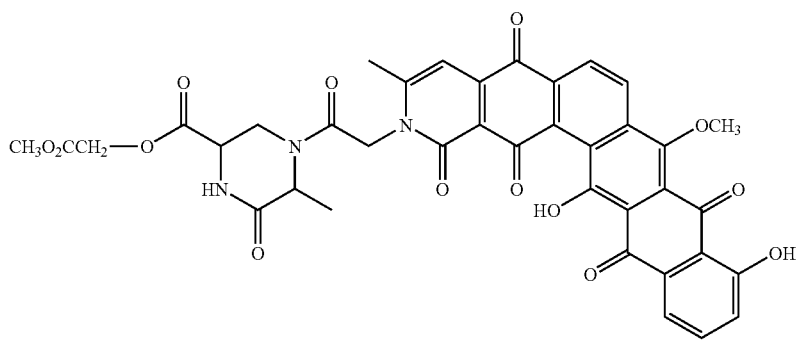

P175-A ETHER A

Example 8B

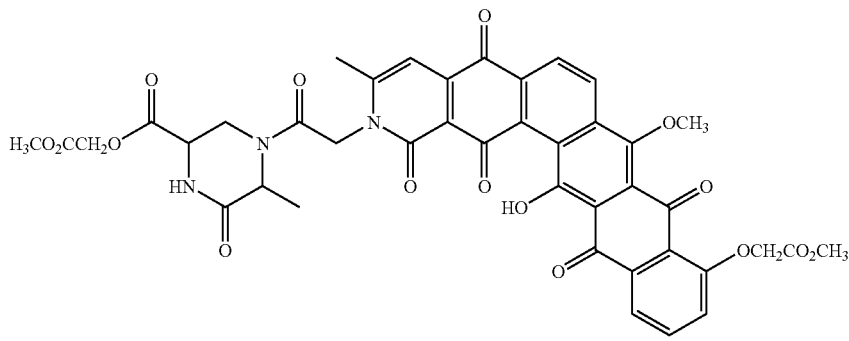

P175A ETHER B

Example 8C

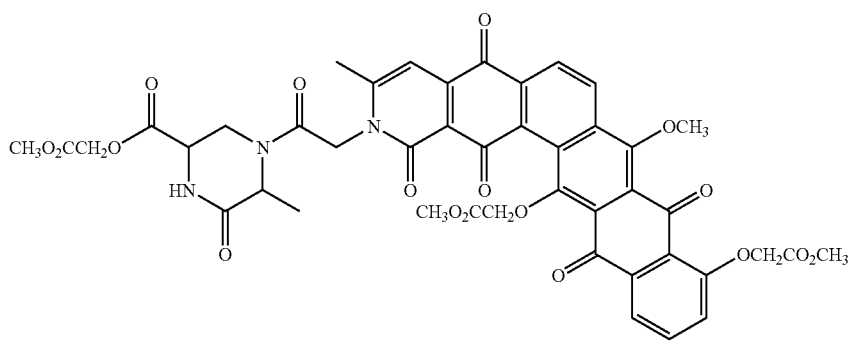

P175A ETHER C

To a solution of P175-A (500 mg) in anhydrous DMSO (10 ml), is added sodium carbonate (1 g) and then bromoacetate methyl ester (1 ml). The reaction mixture was stirred at room temperature for 5 hours. The resulting mixture is filtered. The filtrate is acidified with TFA and then chromatographed by HPLC on the same C18 column as in EXAMPLE 3 using a linear gradient (60–100% acetonitrile in water containing 0.01% TFA in 35 minutes) to afford 3 major products 8A (173.3 mg), 8B (88.1 mg), and 8C (59.0 mg) (FIG. 5). The predominant ESIMS (positive) peaks observed for 8A, 8B, and 8C are respectively at m/z 752, 824 and 896 $(M+H)^+$.

EXAMPLE 9D and 9E

Example 9D

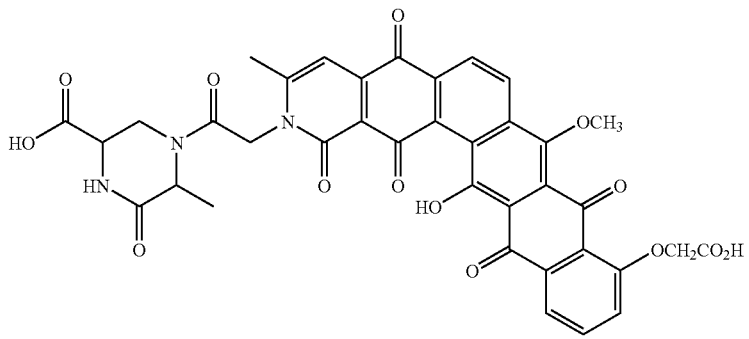

P175-A ETHER D

EXAMPLE 9E

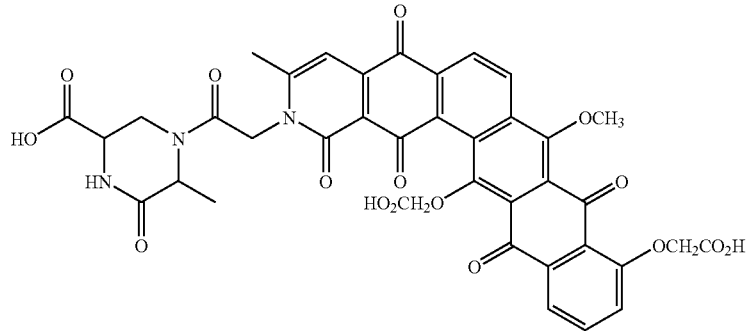

P175-A ETHER E

The products 8A, 8B, and 8C (30 mg each) are respectively dissolved in 2.5% sodium carbonate in 1:1 acetonitrile/water (5.0 ml). The reaction mixtures are stirred at room temperature for 1 hour and acidified with TFA after the hydrolysis is completed. The hydrolysis products are then respectively chromatographed by HPLC on the C18 column (3×250 mm in size) using a linear gradient (20–100% acetonitrile in water containing 0.01% TFA in 18 minutes) to afford products 9D and 9E (FIG. 5) with 35–50% yields. The predominant ESIMS (positive) peaks observed for D and E are respectively at m/z 738 and 796 (M+H)$^+$.

What is claimed is:

1. The compounds of formula I.

Formula 1

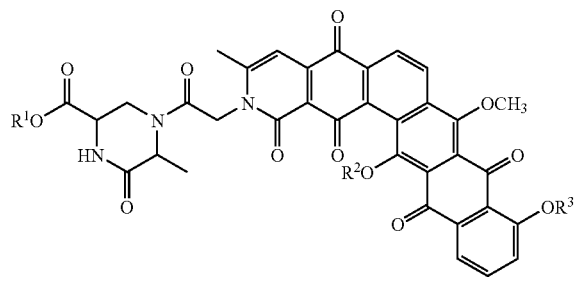

wherein:

R$^1$ is H, straight or branched alkyl of 1 to 10 carbon atoms, cycloalkyl of 3 to 10 carbon atoms,

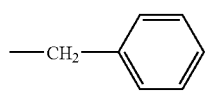

or —CH$_2$COOR$^4$;

R$^2$ and R$^3$ are independently H or —CH$_2$CO$_2$R$^4$;

R$^4$ is H or straight or branched alkyl of 1 to 10 carbon atoms and pharmaceutically acceptable salts thereof.

2. The compounds according to claim 1 wherein:

R$^1$ is —CH$_3$, —CH$_2$CH$_3$, —CH(CH$_3$)$_2$, or

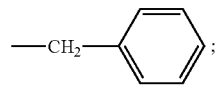

and

R$^2$ and R$^3$ are H.

3. The compounds according to claim 1 wherein:

R$^1$ is H or —CH$_2$COOCH$_3$; and

R$^2$ and R$^3$ are independently H, or —CH$_2$COOCH$_3$, or —CH$_2$COOH.

4. The compounds according to claim 1 wherein:

R$^1$ is H; and

R$^2$ and R$^3$ are independently H or —CH$_2$CO$_2$H.

5. The compound according to claim 1 wherein R$^1$, R$^2$ and R$^3$ are H.

6. The compound which has the structure:

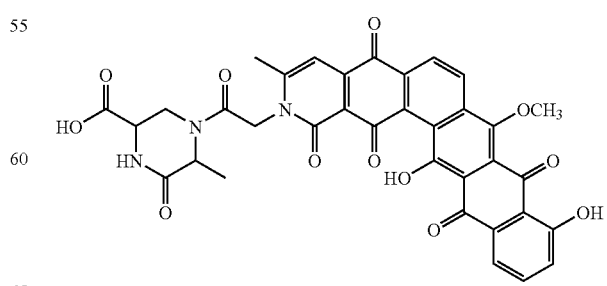

and pharmaceutically acceptable salts thereof.

7. A compound according to claim 1 selected from the group:
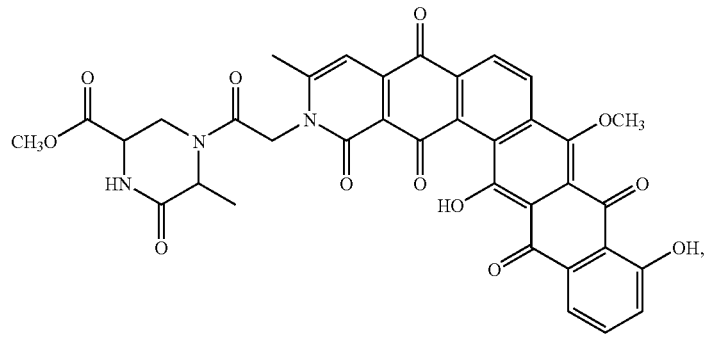
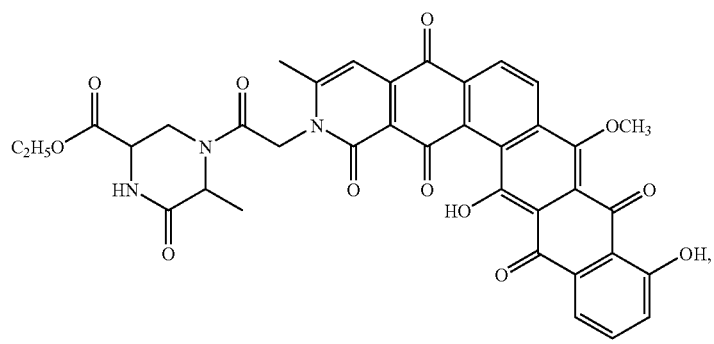
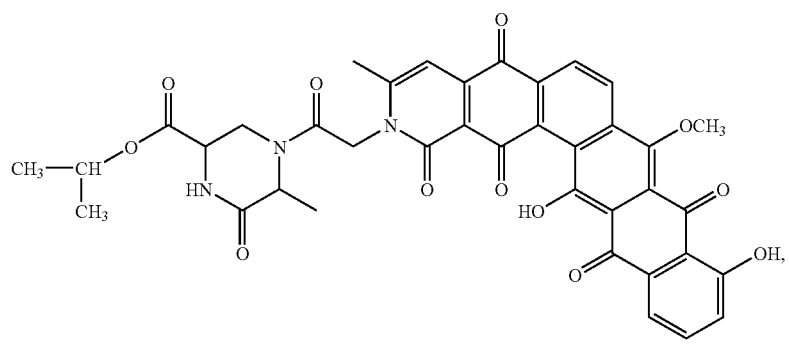
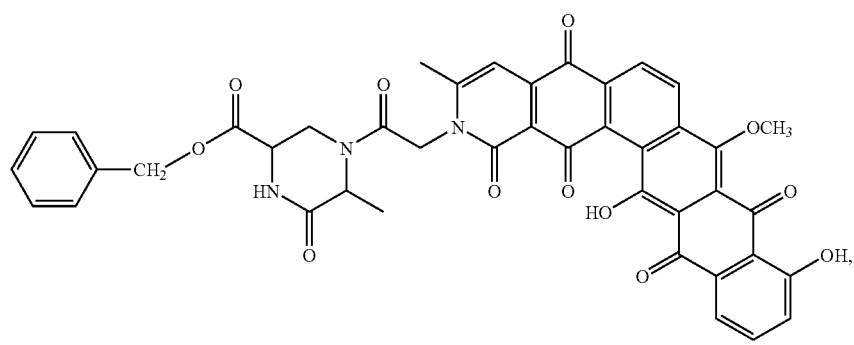

-continued
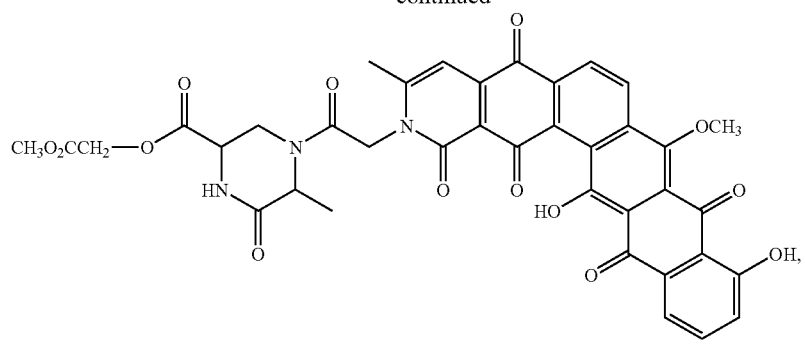
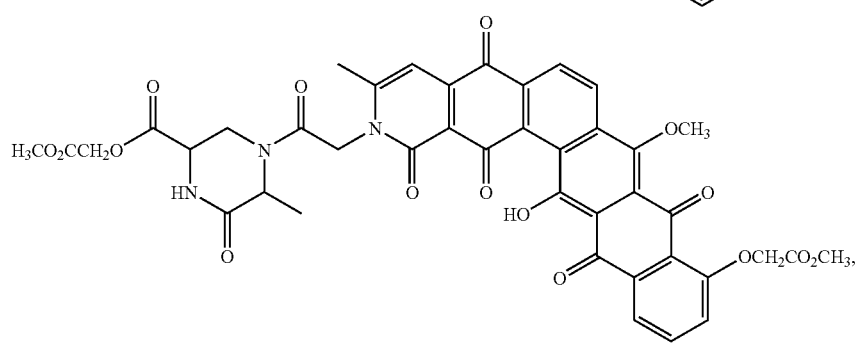
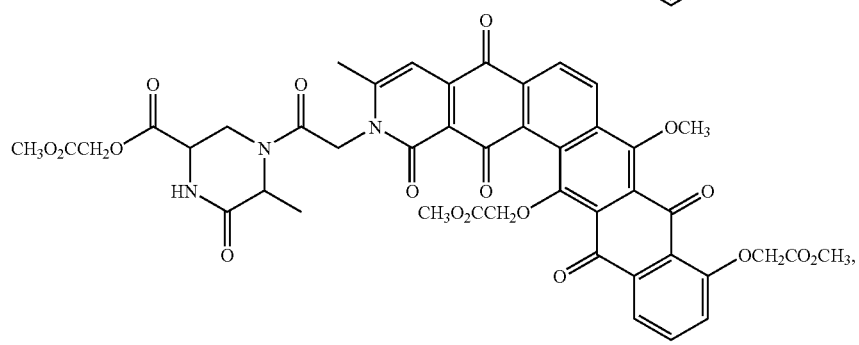
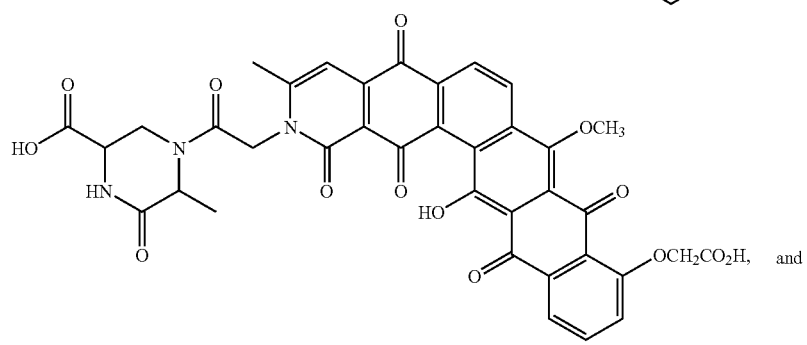
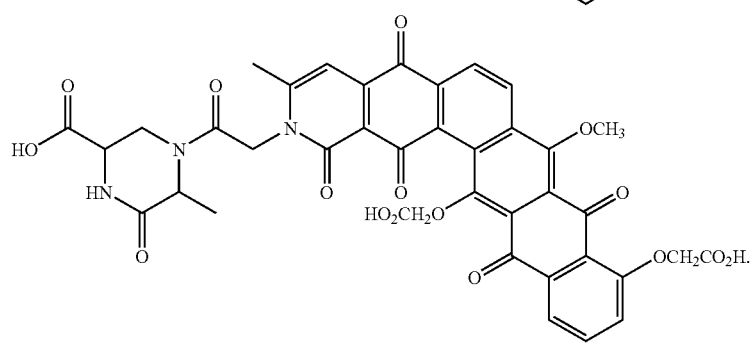

8. A method of treating a warm-blooded animal affected by bacterial infections, which method comprises administering to said warm-blooded animal an effective amount of a compound of claim 1.

9. A pharmaceutical composition comprising an effective amount of a compound of claim 1 together with a pharmaceutically acceptable carrier.

10. A pharmaceutical or disinfectant composition which contains an effective antimicrobial, antiseptic or disinfectant amount of the compound of claim 1 as an active ingredient.

11. A process for the preparation of antibiotic having the structure

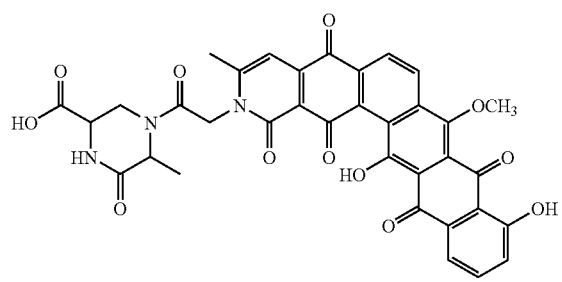

which comprises cultivating *Micromonospora echinospora* designated NRRL 30633 or a mutant thereof capable of producing said antibotic under aerobic conditions in a sterile liquid medium containing assimilable sources of carbon, nitrogen and inorganic anion and cation salts, until substantial antibiotic activity is imparted to said medium by the production of said antibotic and recovering and isolating said antibiotics.

12. A biologically pure culture of *Micromonospora echinospora* NRRL 30633 or a P175-A producing mutant thereof.

13. An antibiotic having the structure

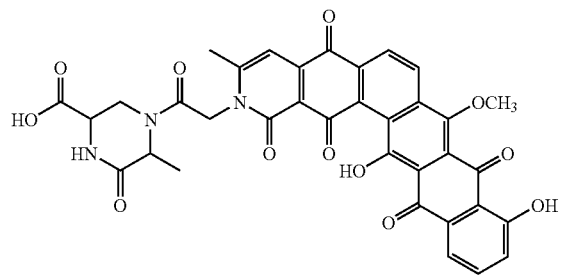

produced by the process which comprises aerobically fermenting the organism *Micromonospora echinospora* NRRL30633 or a mutant thereof capable of producing said antibiotic in a liquid medium containing assimilable sources of carbon, nitrogen and inorganic anions and cations until a substantial amount of said antibiotic is produced in said medium.

14. A process for the preparation of esters having the structure

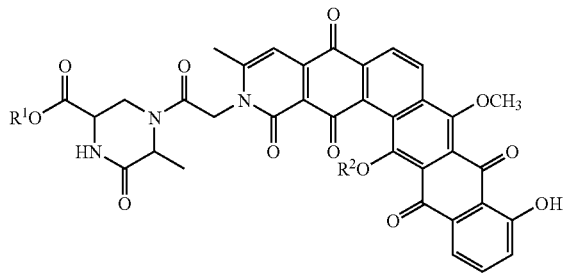

which comprises reacting a compound of the formula

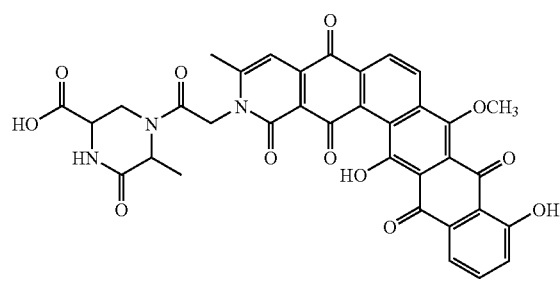

with an alkylating reagent $R^1X$, where X is bromo or iodo and where $R^1$ is straight or branched alkyl of 1 to 10 carbon atoms, cycloalkyl of 3 to 10 carbon atoms,

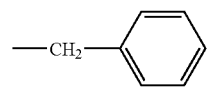

or —$CH_2CO_2R^4$ where $R_4$ is straight or branched alkyl of 1 to 4 carbon atoms in the presence of a base and dimethylsulfoxide to afford esters having the structure

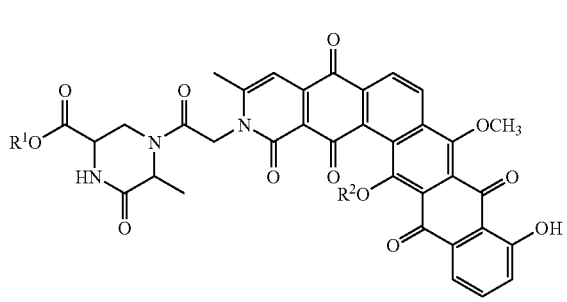

* * * * *